United States Patent [19]
Gambell et al.

[11]  4,085,275
[45]  Apr. 18, 1978

[54] PRODUCTION OF DI-UNSATURATED CARBOXYLIC ACIDS

[75] Inventors: James W. Gambell, St. Louis; H. Burnham Tinker, Creve Coeur, both of Mo.

[73] Assignee: Monsanto Company, St. Louis, Mo.

[21] Appl. No.: 644,984

[22] Filed: Dec. 30, 1975

[51] Int. Cl.² ............................................. C07C 67/30
[52] U.S. Cl. ................................ 560/130; 260/405.5; 260/465.9; 260/526 N; 560/214
[58] Field of Search ............ 260/479 R, 486 D, 465.9, 260/526 N, 405.5

[56] References Cited
U.S. PATENT DOCUMENTS 1,374,589  4/1921  Levey ................................. 260/405.5
2,945,057  7/1960  McDaniel et al. ............... 260/486 D Primary Examiner—Jane S. Myers
Attorney, Agent, or Firm—Joseph D. Kennedy; John D. Upham

[57] ABSTRACT

The invention concerns dehydrogenation of carboxylic acids, lactones, esters, nitriles, the carbon skeleton of the feed material being characterized as containing mono-unsaturation or alternatively functional groups such as hydroxyl which convert under process conditions to unsaturation, the dehydrogenation reaction being conducted in the presence of a contact catalyst comprising a carbonaceous layer effective for the dehydrogenation of mono-unsaturated reactants to di-unsaturated products. Another aspect of the invention involves production of the mono-unsaturated reactants. In particular, the invention provides a route to sorbic acid, for example by dehydrogenation of hexenoic acids or esters thereof.

21 Claims, No Drawings

PRODUCTION OF DI-UNSATURATED CARBOXYLIC ACIDS

The present invention relates to the dehydrogenation of unsaturated carboxylic acids, lactones, esters or nitriles, particularly to the dehydrogenation of hexenoic acid esters to hexadienoic acid esters.

BACKGROUND OF THE INVENTION

Sorbic acid is a material of known commercial uses which is available through a process based on the reaction of ketene with crotonaldehyde. The process is effective but its economics depend upon the cost and availability of reactant materials and is also encumbered with formation of undesirable tars. Various dehydrogenation processes are known for dehydrogenating alkanes to alkenes and alkenes to alkadienes as well as some oxidative dehydrogenation processes disclosed as dehydrogenating saturated acid esters to alkenoic acid esters, see U.S. Pat. No. 3,652,654. Various dehydrogenation catalysts are also known.

SUMMARY OF THE INVENTION

The present invention is directed to the production of di-unsaturated acids or esters (alkadienoic acids or esters) by the dehydrogenation of carboxylic acids or esters containing mono-unsaturation, or alternatively reactants capable of being converted to mono-unsaturated acids or esters such as lactones or unsaturated nitriles. The dehydrogenation reaction of the present invention is conducted at elevated temperature in the presence of a catalyst comprising a carbonaceous layer effective for the desired dehydrogenation reaction to di-unsaturated products.

DETAILED DESCRIPTION OF THE INVENTION

The present invention is concerned with the production of di-unsaturated acids or esters from reactants containing mono-unsaturation such as alkenoic acids or esters, or alternatively from reactants containing functional groups capable of being converted in the course of the dehydrogenation reaction to mono-unsaturated species. Another aspect of the present invention involves means for production of the desired reactants for the dehydrogenation reaction. Thus, the reactant to be dehydrogenated is characterized by containing therein both the mono-unsaturation aspect and the carboxylic acid or ester aspect. The mono-unsaturation aspect may be exemplified by a carbon-to-carbon double bond. Alternatively, hydroxyl groups can be dehydrated to double bonds. The dehydration can occur during the dehydrogenation reaction or can be conducted in a separate step prior to the dehydrogenation reaction. The carboxylic acid or ester aspect can be exemplified by a carboxylic acid ester or acid moiety itself; alternatively, the carboxylic acid or ester grouping can be generated from another functional grouping such as a lactone or nitrile. In the latter case, the lactone or nitrile can be employed in the dehydrogenation reaction or be converted in a previous step.

The presence of the mono-unsaturation aspect and the carboxylic acid or ester aspect is significant to the practice of the present invention. In the present invention, carboxylic acid esters not containing the mono-unsaturation aspect do not dehydrogenate to the desired di-unsaturated product. Rather, a Claisen Ester Condensation or related condensation reaction can occur. Very little, if any, di-unsaturated product is obtained.

In contrast, in the present invention reactants containing both the mono-unsaturation aspect and the carboxylic acid or ester aspect dehydrogenate readily at elevated temperature in contact with catalysts utilized in the present invention to produce di-unsaturated products.

The catalysts when catalyzing dehydrogenation in the present invention comprise a carbonaceous layer deposited on suitable catalysts or supports and this constitutes a particular aspect of the present invention. It has been found that reactants containing the mono-unsaturation aspect and the carboxylic acid or ester aspect do not dehydrogenate to desired di-unsaturated products when simply passed over catalysts at elevated temperatures conducive to dehydrogenation. Rather, an induction period is observed wherein little if any desired di-unsaturated product is obtained. During the induction period, a carbonaceous layer is deposited on the contact catalyst or support. When the carbonaceous layer build-up becomes effective the desired di-unsaturated products are observed.

In a preferred process of the present invention to hexadienoic acids or esters thereof, a hydrocarbon feed is employed at elevated temperatures as illustrated hereinafter to produce an effective carbonaceous layer. The production of hexadienoic acids or esters can then employ as reactants materials capable of forming di-unsaturated $C_6$ acids or esters. The desired trans, trans 2,4-hexadienoic acid (sorbic acid) or its ester is readily produced in significant yields by employing as reactant 2-hexenoic acid or an ester thereof. However, since considerable double bond isomerization is observed in the hexadienoic products and also with unreacted 2-hexenoic feed, other hexenoic acids or esters can be employed such as the 3-hexenoic acid, 4-hexenoic acid or 5-hexenoic acid or esters thereof. The products of the dehydrogenation reaction will not necessarily be the same and in any case a mixture of hexadienoate isomers will be formed. Thus, another aspect of the invention involves separation and purification of the product hexenoates and hexadienoates.

The process illustrated herein produces other position isomers along with the 2,4-alkadienoic acid esters which are preferred in the case where the mono-unsaturated starting material is a six-carbon alkenoic ester. The other position isomers, however, are amenable to isomerization to the 2,4-isomers, e.g., during the course of the dehydrogenation process. Alternatively, the product of the dehydrogenation process can be treated to convert the various position isomers to the desired form. Various isomerization techniques known in the art can be employed. For example, with a six carbon alkenoic acid ester reactant the reaction product containing the various alkadienoic position isomers can be isomerized to the desired 2,4-isomers under mildly basic conditions at slightly elevated temperature. One means of accomplishing the desired isomerization employs catalytic amounts of base, e.g., NaOH, in methanol at about 40° C.

The present process is of particular interest for dehydrogenation of hexenoic acid esters as a route to sorbic acid (trans, trans, 2,4-hexadienoic acid) but other mono-unsaturated reactants can also be employed within the scope of the present process. Of course, in order to produce a product containing two non-adjacent double bonds the reactant must contain at least five carbon atoms. In general, mono-unsaturated acids of at least 5 carbon atoms or their esters, or lactone, or nitrile precursors are suitable in the present process.

The present process is directed toward dehydrogenation of mono-unsaturated carboxylic acids, lactones, esters or nitriles. The preferred ester portion of the reactant will ordinarily comprise a group consisting of methyl, phenyl or other radicals which are characterized as lacking labile hydrogen on the beta-carbon of the alcohol group. With alcohol groups containing labile hydrogen in the beta-position, for example the ethyl grouping, an ester pyrolysis reaction can occur to give the acid itself and in the case of the ethyl grouping, ethylene. The ester pyrolysis reaction therefore leads to a loss of the alcohol group and generation of light ends. Any ester grouping which is stable under the dehydrogenation conditions as taught herein can be employed with advantage.

Alkenoic acids themselves can be employed in the present invention. Results will not necessarily be the same as with esters thereof. However, certain advantages may accrue, for example, through simpler product separation or through the removal of the step of saponifying an ester or ester mixture to obtain the acid or acids.

Nitriles can be employed in the present invention. The presence of a nitrile function can, however, result in a reactant which is more difficult to dehydrogenate. By this is meant, in part, that the thermodynamics of nitrile dehydrogenation may not be as favorable as the thermodynamics for dehydrogenation of acids or esters. This can result in lower conversions per pass to di-unsaturated species.

Alkanoic acids, esters or nitriles containing hydroxy groups can be employed in the present invention. Under dehydrogenation conditions as illustrated hereinafter dehydration can occur to yield a double bond in situ. Alternatively, the dehydration can be conducted prior to the dehydrogenation reaction.

Production of suitable reactants for dehydrogenation to alkadienoic final products can be achieved by a variety of means. The following is meant to be illustrative of possible routes to mono-unsaturated starting materials and should not be considered as limiting the scope of the present invention.

1. Carbonylation of piperylenes.

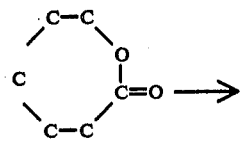

2. Dehydration of caprolactone,

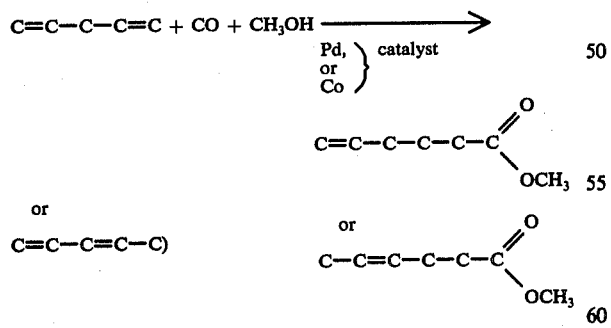

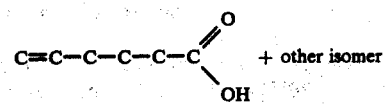

A methanol diluent could be employed to advantage.

3. Dehydration of other lactones,

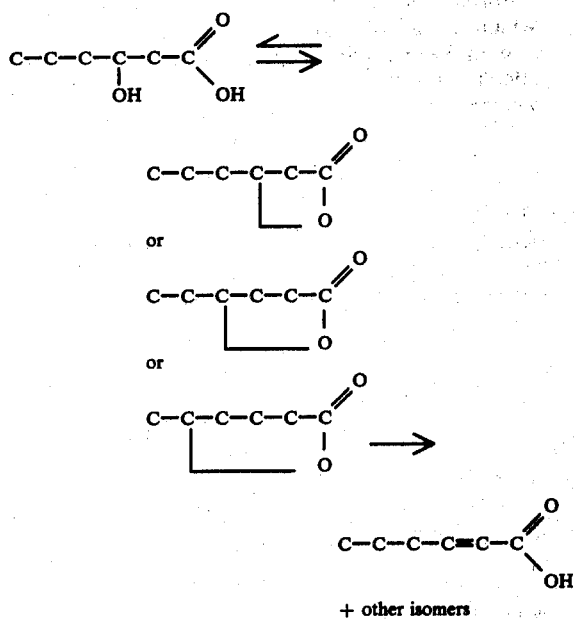

A methanol diluent could be employed to advantage.

4. Hydroformylation of piperylenes followed by oxidation.

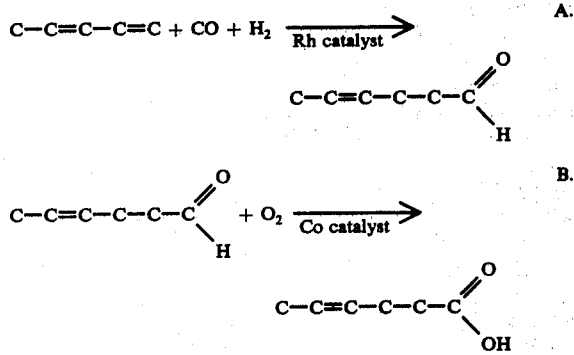

The mono-unsaturated acid (or ester) would be employed as taught herein in the dehydrogenation step.

5. Hydroformylation and cyanohydrin formation

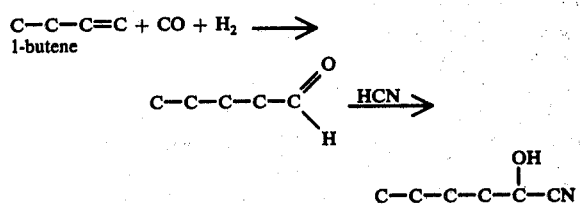

The cyanohydrin could be hydrolyzed, viz.:

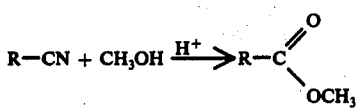

The above ester could be dehydrated as taught in the process of the present invention.

6. Selective hydrogenation of adipic acid

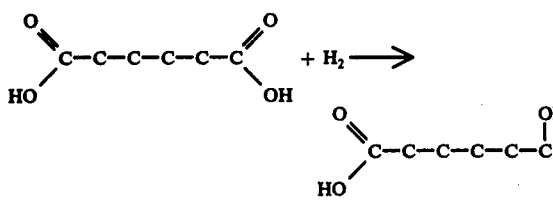

The resulting 6-hydroxy hexanoic acid can be dehydrated

7. Hydrocyanation of piperylenes

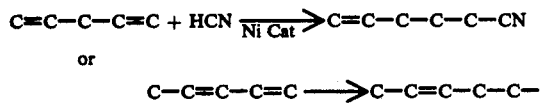

The unsaturated nitrile would be processed as taught hereinabove.

8. Thallium oxidation of hexanoic acid.

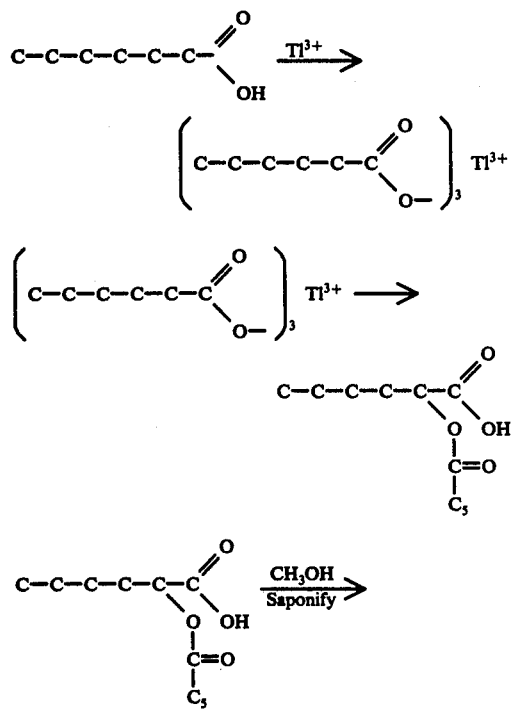

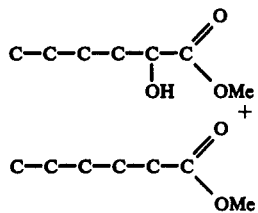

The hydroxy acid would be dehydrated as described hereinabove.

It is understood, of course, that equivalent results will not be obtained with the various processes taught immediately hereinabove. The choice of process to employ will depend on factors such as availability of raw materials and other economic considerations based on number of reaction steps, per-pass-yields, separation costs and the like. It will be understood that the carbon atoms in the skeletal formulae are tetravalent and that the valence bonds not shown are attached to hydrogen. Production of alkadienoates of different carbon numbers than illustrated above will require use of reactants of appropriate carbon number.

The present invention involves a simple dehydrogenation of an alkenoic acid, ester or nitrile to the corresponding di-unsaturated species. The dehydrogenation is conducted under usual catalytic dehydrogenation conditions. The dehydrogenation reaction is promoted by elevated temperatures with the dehydrogenation rate generally increasing with temperature. The temperatures employed will generally be over 350° C, say in the range of about 400° C to about 600° C or slightly higher, preferably in the range of about 450° C to about 550° C, with some variance depending upon the activity of the catalyst, reaction dwell time, etc. In some instances it may be advisable to increase the reaction temperature as the reaction proceeds in order to compensate for catalyst deactivation.

The present process is conducted over a solid contact surface serving as a dehydrogenation catalyst. Metals, and to a lesser degree metal oxides and salts derived therefrom are known as dehydrogenation catalysts, as well as carbon and other carbonaceous materials. Suitable carbonaceous materials for dehydrogenation are deposited on solids when hydrocarbon or other carbon-containing materials contact such solids at high temperature. This results from coking or cracking reactions of the materials producing a coke like or similar carbonaceous materials, presumably composed primarily of carbon and hydrogen in varying ratios. Such carbonaceous deposit can be produced by contacting a particulate solid with gaseous organic compounds at temperatures upwards of 500° C, for example 400° to 600° C or higher. The alkenoic acid ester reactant can itself serve as the source of the carbonaceous deposit. For example, the present reaction can be carried out by conducting an alkenoic acid ester over a particulate or other high surface area solid at high temperature as illustrated further in examples contained herein for an induction period to permit formation of a carbonaceous deposit, and then continuing the procedure to produce alkadienoic acid ester.

Other organic compounds can be employed as illustrated hereinbelow. Thus, organic compounds can be selected from the illustrative list which includes paraffins, olefins, alkynes, aromatic compounds, carboxylic acids and esters thereof, nitriles, lactones, alcohols. It is of course understood that the organic compound selected must be amenable to the carbon deposition reaction as taught herein, for example suitably volatile at about 400° C to 600° C. It is also understood that choice of organic compounds will be dependent on other factors such as process economics as taught herein. Results obtained will not necessarily be equivalent and will depend on a variety of factors including contact catalyst employed, reactant compound employed in the dehydrogenation process thereafter among other factors.

The listing above is meant to be illustrative only and is not considered to limit the scope of the present invention as taught herein.

While a wide variety of organic compounds can be employed to deposit a carbonaceous layer effective for the dehydrogenation process taught herein, we have utilized selected compounds from the above list with success. For example, olefins such as butenes can be used. In addition, reactant compounds of the present invention can be used. Generally speaking, those organic compound feeds useful in the generation of effective carbonaceous layer can be characterized as depositing carbonaceous layers effective for the dehydrogenation of hexenoate esters, in particular methyl hexenoates and even more specifically methyl 2-hexenoate.

Any type of solid surface can be employed, so long as it does not react with the reactant employed to an undesirable extent, i.e., a carbonaceous layer suitable for dehydrogenation is achieved which does not produce undesirable by-product formation. Thus the surface can be inert, or of the type regarded as catalytically active. For example, surfaces commonly used as catalyst support surfaces can be used, for example, clays, pumice, kieselguhr, alumina, carbon, silicas, etc, whether such surfaces have activity in themselves, or only from deposition of carbonaceous material thereon. While inert materials can be employed, it is generally desirable to employ a material with some dehydrogenating or cracking activity in order to minimize the induction period to produce a carbonaceous deposit. When a carbonaceous deposit has been produced, other dehydrogenation sites in the catalyst may for the most part be unavailable. However, the various known hydrogenation-dehydrogention catalyst materials can be used, such as platinum, palladium and the other noble metals, nickel, copper and their oxides, etc., and the various activated aluminas. However, some such catalysts have substantial cracking activity, and it is preferred to minimize such activity, making it generally desirable to avoid platinum or acidic catalysts, and rather to utilize catalysts which have high selectivity for dehydrogenation, for example chromia on alumina catalyst, nickel calcium phosphate catalysts, and the like. Catalysts effective for dehydrogenating paraffins such as butane, or olefins such as butenes, particularly the commercially employed catalysts for such dehydrogenations can be used. For example the Houdry chromia alumina catalyst, the Standard Oil Development 1707 type catalysts of magnesium, iron and copper oxides, e.g., 80% MgO, 20% Fe$_2$O$_3$ and 5% CuO, the Dow nickel calcium phosphate catalyst, Ca$_8$Ni(PO$_4$)$_6$ stabilized with chromium oxide. Various dehydrogenation catalysts taught in treatises on catalysts can be employed, for example those taught in Catalysis, III, Hydrogenation and Dehydrogenation, Emmett (Reinhold 1955), particularly on pages 470–479, with description of catalysts on pages 472–475, including variations in the 1707 type catalyst in a Table on page 475, and a description of preparation of the Dow catalyst; also see the description of dehydrogenation processes and various catalysts on pages 458–466, including listings of various catalyst compositions and discussion of commercial processes. The described catalysts are generally suitable for use in the present invention. Various aspects of dehydrogenation procedures are further discussed in Monoolefins; F. Ansinger, Pergammon Press (English Ed. 1968), pages 70–80, and the various procedures for dilution, lowering pressure, supplying heat, etc., can be employed in the present invention, as well as the catalysts, for example, the Houdry catalyst described as active alumina containing 18–20% chromium oxide.

The temperature employed in the process will be those sufficient to obtain dehydrogenation at an acceptable rate, with the rate increasing with increasing temperature, appreciable reaction rates occurring with certain possible reactants of the present invention at temperatures of about 400° C or higher. There will be some variation in the rate depending upon the catalyst, concentration and other factors. In general it will not be desirable to exceed 600° C or so because of the tendency toward cracking or other reactions leading to sideproducts. Fixed beds, moving beds, or various other expedients used in catalytic processes to effect gas-solid contact can be employed. Catalyst bed size and flow rate or other measure of throughput can be determined as desired to have the appropriate accommodation of conversion, yield and process economics.

It is, of course, understood that the conversions and product distributions obtained in conducting the present process can be equilibrium limited. For example, the maximum conversion to alkadienoic acid ester will be a function of the particular reactant alkenoic acid ester, reaction temperature, space velocity, diluent if any, pressure among other factors. Space velocities can be started in terms of total gas flow or on the basis of reactant alkenoic acid ester. The relationship between the two is well known in the art. The present process can be conducted, for example, by utilizing reduced partial pressure of reactants achieved by use of partial vacuum operation or by use of diluents. For example, an inert diluent can be employed such as nitrogen or the like at a volume ratio of diluent to reactant of 0:1 to 50:1 or even higher, the total pressure being about atmospheric. Space velocities based on total gas flow will generally be in the range of about 50 to 5000 hr$^{-1}$, preferably in the range of 100 to 1000 hr$^{-1}$. The choice of diluent-:reactant ratio and space velocity will depend, in part, on choice of diluent composition.

The present process proceeds well with only the reactant, contact catalyst and optionally inert gases present, and no oxidizing agents of the type used in oxidative dehydrogenating reactions are necessary. However, small amounts of oxygen such as 2 or 3% or so by volume can be present and may even be beneficial in promoting the reaction by converting the hydrogen generated to water, or in slowing the pace of catalyst deactivation during the reaction. Polymerization or other carbonization reactions tend over the course of a reaction to occlude catalyst sites, and regeneration will be appropriate as in dehydrogenation processes in general. Oxygen can be used for such regeneration and its use is generally indicated, particularly for metallic catalysts on the usual inert supports. However, carbon catalysts or supports or other combustile supports are not generally amenable to such regeneration, and this should be considered in selecting catalysts and supports. If desired, the type of catalysts employed in oxidative dehydrogenations, such as those containing iron, lead phosphate, antimony, arsenic or bismuth and the like can be employed in the present process.

Hydrogen can also be employed in the present process, for example to maintain catalyst activity for longer periods of time. It is of course understood that there will exist an optimum amount of hydrogen which can be used which can vary with reactant systems and catalyst systems employed. It is also understood that the use of small amounts of oxygen as taught herein and use of hydrogen will not be employed in the same reaction. Hydrogen may be employed along with an inert diluent or may comprise the diluent totally.

Water can also be employed in the present process, for example to maintain catalyst activity for longer periods of time. It is apparent that with certain of the reactant compounds of the present invention, for example those undergoing dehydration to form water during the course of the dehydrogenation reaction, water can be formed. Combinations of water, inert diluent, oxygen or hydrogen are possible, or water may comprise the diluent totally.

EXAMPLE 1

Ten cc of the selected catalyst, 14 × 20 mesh, was tamped into a 17 mm I.D. quartz tube with a bed length of about 5 cm. A 6 mm O.D. thermowell ran through the center of the catalyst bed from the bottom. The reactor was heated by a resistance type furnace, and the inlet line was heated by heating tape. The ester reactant was fed from a saturator vessel containing liquid ester, using a nitrogen sparge. A typical nitrogen flow was 100 cc per minute. The saturator vessel was heated to 55°–95° C or so to vary the vapor pressure of the ester reactant. The exit tube of the reactor lead to a liquid collection vessel, which was vented to a water-cooled condenser, followed by two dry-ice cooled traps. The collection system was not adapted to collect such compounds as dimethyl ether, methane, ethane, other light ends which would escape from the traps.

In the system described above, Houdry 25-Z chromia alumina catalyst was employed and the catalyst was contacted by a dilute stream of methyl isobutyrate at 600° C until the catalyst was activated as evidenced by methyl methacrylate production, and the feed was switched to methyl 2-hexenoate. The mole percent of ester in the reaction stream was 4.8 and the space velocity was 650 reciprocal hours. There was substantial conversion to methyl hexadienoates, along with substantial isomerization of the methyl 2-hexenoate. The liquid recovery was low, indicating that the temperature employed was undesirably high for initial phases of a run; the liquid collection vessel contained about 20% cracked products, and about 30% hexadienoates. When the temperature was dropped to 500° C, the hexadienoates decreased to 8% in the liquid recovered but there was also a marked drop in isomerization and very little cracking as shown by practically complete recovery in the liquid collection vessel. When the temperature was increased to 550° C the conversion was increased to 14%. When dehydrogenation of methyl hexanoate, a saturated acid ester, was attempted under similar conditions, no significant quantities of any desired unsaturated esters were found, and products were identified which apparently resulted from a Claisen Ester Condensation followed by decarbonylation (e.g., a major product was identified as an eleven carbon ketone.) When a carbon on alumina catalyst was substituted for the chrome alumina, and employed with methyl hexanoate reactant, a similar result was obtained. However, the catalyst was activated more quickly, that is, a shorter induction period was utilized. The conversion rate over this catalyst appeared lower than over the chrome alumina. The carbon on alumina catalyst in the form of 5 to 8 mesh spheres was prepared by depositing finely divided carbon (~30 wt. %) on activated alumina (KA-101) by passing 1-butene in nitrogen over the support at elevated temperature (~450° C).

Similar results to those with methyl 2-hexenoate can be obtained by substituting in place of methyl-2 hexenoate as reactant, 2-hexenoic acid, 3-hexenoic acid, caprolactone, hydroxycapronitrile, hydroxycaproic acid, or the methyl ester of 3-hydroxyhexenoic acid. The corresponding hexadienoic acids, or nitriles or their isomers are obtained.

EXAMPLE 2

A Dow-B calcium nickel phosphate catalyst was employed, an 8.78 gram amount being utilized in the reactor and with the general procedure of Example 1. Methyl 2-hexenoate was utilized for activation at 500° C till hexadienoate production was observed after 1.25 hours after which a 6-hour run was then made at that temperature at a space velocity of 650 reciprocal hours. Concentration of the reactant was 5 mole %. About 87% of the reactant fed was recovered in the liquid collection vessel, with about 22% of the liquid recovered being hexadienoates, with the balance the hexenoate feed or its position isomers. The product distribution was relatively constant during the 6 hour reaction. Considering the hexenoate isomers as recovered reactant, the selectivity to hexadienoates is about 90% or better.

EXAMPLE 3

A run was made as in Example 2 but employing about twice the amount of catalyst, 18.3 grams, and a slower reactant feed rate, initially 0.87 gram per hour. The catalyst was activated with methyl 2-hexenoate at 500° C, 325 hr$^{-1}$ for 3.5 hours. After the induction period, operation was at 500° C and 150 reciprocal hours; the material recovery in the liquid collection vessel was typically around 50% with around 32% of the liquid product collected being hexadienoates, for approximately a net conversion to total hexadienoates of 15%. Of course this ignores any hexadienoate or other material which may have been recovered in the cold traps. When the temperature was raised to 550° C after 7½ hours, the liquid collection vessel recovery declined to 24%, but with 54% being hexadienoates. On lowering the temperature to 500° C, and then doubling the space velocity (to about 300 reciprocal hours) and raising the temperature to 525° C, the liquid recovery was about 90% with 25% hexadienoates for a net conversion of about 22%. A further rise to 550° C slightly increased the hexadienoates in the liquid product for an effective conversion of approximately 30%.

The examples given illustrate a process for the production of hexadienoate esters, which are useful in themselves or by isomerization and saponification to sorbic acid. Of the eight possible methyl hexadienoate isomers, five chromatographic peaks were found and identified by gas chromatography-mass spectroscopy interface as hexadienoates. The sorbate ester, i.e., the methyl ester of trans, trans-2,4-hexadieonic acid was definitely identified by comparison with an available authentic sample. Of the other possible isomers, some would not be expected to result from the process taught herein; other hexadienoate isomers likely observed included cis,trans-2,4-hexadienoate, of trans, cis-2,4-hexadienoate. Further quantitative analysis by area percent of a sample of liquid product from Example 3 to determine the amount of sorbate ester compared to other isomers showed 13% sorbate and 17% other hexadienoates by one chromatographic method of analysis, along with 30% 2-hexenoate feed and 35% other hexenoate isomers. A second analytical method gave 22% sorbate to 11% other hexadienoates, and 31% 2-hexenoate to 34% other hexenoates.

The first analytical method used a Hewlett-Packard 7620A chromatograph using flame ionization detection. A 50 ft. coated open tubular column was used with a coating of Carbowax 20M/AgNO$_3$ and temperature programmed from 70° C to 180° C at 6° C/min. (Carbowax 20M is a trademark for a high molecular weight polyethylene glycol of ~20,000 M.W.) Samples of 0.05 to 0.1 microliter were injected directly onto the column. The method was intended for high resolution of the various hexenoate and hexadienoate isomers. The second analytical method was intended for routine analysis of liquid product fractions, particularly to determine total hexadienoates along with other components, including possibly free acids. The product distributions reported herein were generally determined by this method. The method used a Hewlett-Packard 5754-B or 5750 chromatograph using thermal conductivity detection. The column was a 12 ft. by ⅛ inch stainless steel column with 10 wt. % UCW-98 on silanized Chromosorb S. (UCW-98 is a trade designation for a liquid phase silicone and Chromosorb W is a trademark for a flux-calcined white diatomite aggregate). Unless otherwise indicated, the percentages in product determinations herein are percentages by weight.

Methyl sorbate itself is subject to some reaction or isomerization under the reaction conditions employed herein. For example, methyl sorbate at a concentration of 3 mol percent was conducted over the catalyst of Example 3 at 500° C and space velocity of 650 hr$^{-1}$. Analysis of the liquid collection vessel content after 2.5 hours showed 3% methyl 2-hexenoate, 10% other hexenoate isomers, and 84% hexadienoates. Of the hexadienoates, about 30% consisted of isomers other than the starting sorbate.

The hexadieonate esters produced in the present invention can be separated from reactants and recovered by distillation and, as indicated, the various isomers can be isomerized to the sorbate form and saponified to sorbic acid. Other alkadienoic esters are amenable to similar treatment, but the ultimate product will, of course, be a homolog of sorbic acid. If desired, the isomers can be separated by such absorption procedures as utilized in chromatography but this is not likely to be done in practice. Other means of purifying sorbic acid known in the art such as relying on the pronounced insolubility of sorbic acid relative to other hexadienoates can be employed.

The present process is viewed as involving the abstraction of hydrogen from a mono-unsaturated acid, lactone, ester or nitrile reactant with the metal oxide, carbonaceous deposit or similar material serving essentially only as a catalyst rather than as a stoichiometric reactant. Moreover oxygen or other oxidizing agents in stoichiometric amounts are not needed to oxidize the reactant, as the catalyst dehydrogenation occurs in the absence of such stoichiometric oxidizing agents as oxygen, some metal oxides, and the like. Procedures not needing such oxidizing agents can be termed "nonoxidative dehydrogenations" in contrast to those termed "oxidative dehydrogenations" which require oxidizing agent in stoichiometric quantity. The present invention can utilize catalysts and conditions which are not suitable for dehydrogenating saturated acids, i.e., alkanoic acids.

The present process provides a convenient and relatively simple method for converting mono-unsaturated-acids, -esters, -nitriles, and lactones to di-unsaturated products, largely free from hard to separate contaminants, and particularly for converting hexenoic acid or its esters to sorbic acid or its esters. Thus a novel and useful route to such useful unsaturated acids as sorbic acid is provided. Other di-unsaturated acids in the C$_5$ plus range are likewise produced readily.

The carbonaceous layer which is effective in the present invention is characterized by being effective for dehydrogenating alkenoic esters, and it has been discovered in the present invention that such unsaturated esters are susceptible to dehydrogenation over the carbonaceous layer, while alkanoic esters are not generally dehydrogenated by such catalyst. An effective carbonaceous layer for dehydrogenating alkenoic esters (and hence effective for converting alkenoic acids, alkenoic esters, alkenonitriles, hydroxyalkanoic acids, hydroxyalkenonitriles, as well as alkanolactones, to di-unsaturated acids, esters and nitriles) can be formed by conducting any of the aforesaid reactant compounds over a solid contact material, especially over a selective dehydrogenation catalyst, at elevated temperature, for a sufficient time to form such carbonaceous layer as evidenced by commencement of dehydrogenation to di-unsaturated acids, esters and nitriles. In such process the reactant compound will have at least a five carbon atom chain, in the acid or nitrile function to provide a site for 2,4- or other unsaturation in the product. It will be understood that alkenonitriles and alkadienonitriles have reference to R—CN; R is an alkene or alkadiene. The reactant compounds utilized in the present process will usually have 5 to 8 or 10 carbon atoms, but reactants of higher carbon numbers can be utilized.

What is claimed is:

1. A process for the production of five carbon chain length or greater alkadienoic acids and esters thereof and alkadienonitriles which comprises contacting reactant compounds having a carboxylic acid or nitrile function of 5 to 10 carbon atoms from the group consisting of alkenoic acids and esters thereof, in which the ester group is stable under the dehydrogenation reaction conditions used in the process, alkenonitriles, hydroxylalkanoic acids and esters thereof, in which the ester group is stable as aforesaid, hydroxynitriles and lactones of hydroxy-alkanoic acids with a solid contact catalyst comprising a carbonaceous layer, produced by contacting a solid with organic compounds at high temperatures, effective for the dehydrogenation of methyl hexenoates to methyl hexadienoates at elevated temperatures of about 350° C to 600° C and space velocities in the range of 50 to 5,000 hr$^{-1}$ and diluent to reactant compound volume ratios in the range of 0:1 to about 50:1 or higher.

2. The process of claim 1 in which alkenoic acids, esters or nitriles are conducted over the solid contact catalyst to form alkadienoic acids, esters or nitriles.

3. The process of claim 1 wherein the reactant compounds are hexenoic acids or ester thereof, or hexenonitriles.

4. The process of claim 1 wherein the reactant compounds are hydroxyhexanoic acids or esters thereof, or hydroxyhexanonitriles.

5. The process of claim 1 wherein the reactant compounds are lactones derived from hydroxyhexanoic acid.

6. The process of claim 1 wherein the reactant compound is methyl or phenyl hexenoate.

7. The process of claim 1 wherein the reactant compound is caprolactone.

8. The process of claim 1 wherein the reactant compound is 6-hydroxyhexenoic acid and esters thereof.

9. The process of claim 1 wherein the contact catalyst comprising a carbonaceous layer is further characterized as being deposited at elevated temperature of about 400° C to about 600° C from a group of organic compounds comprising paraffins, olefins, alkynes, aromatic compounds, reactant compounds and products and ester groups if present in the reactant compound are characterized by lack of labile $\beta$-hydrogen atoms.

10. The process of claim 9 in which the carbonaceous layer is formed on a dehydrogenation catalyst.

11. The process of claim 10 in which the catalyst comprises chromia alumina, alumina, calcium nickel phosphate, iron oxide or promoted iron oxides.

12. The process of claim 1 wherein the solid contact catalyst is further characterized as comprising an activated support material selected from the group consisting of alumina, silica, clays, pumic, kieselguhr, carbon.

13. The process of claim 1 in which a carbonaceous layer is formed by contacting the reactant compound with a high surface area solid for an induction period and di-unsaturated produced is then formed by continuing the contact.

14. The process of claim 1 wherein the diluent is further characterized as comprising an inert gas such as nitrogen.

15. The process of claim 1 wherein the diluent is further characterized as comprising an inert gas with up to 2 to 3 volume percent oxygen.

16. The process of claim 1 wherein the diluent is further characterized as comprising an inert gas with optional amounts of hydrogen.

17. The process of claim 1 wherein the diluent is further characterized as comprising an inert gas with optional amounts of water.

18. The process of claim 1 wherein the diluent is further characterized as consisting essentially of hydrogen.

19. The process of claim 1 wherein the diluent is further characterized as consisting essentially of water.

20. The process of claim 2 in which an alkenoic acid or phenyl or methyl ester thereof is employed.

21. The process of claim 10 in which an alkenoic acid or phenyl or methyl ester thereof is employed.

* * * * *